(12) United States Patent
Cudak et al.

(10) Patent No.: US 9,492,576 B1
(45) Date of Patent: Nov. 15, 2016

(54) DISPLAY SCREEN WITH LIGHT-EMITTING DIODES FOR ULTRAVIOLET DISINFECTION

(71) Applicant: Lenovo Enterprise Solutions (Singapore) Pte. Ltd., Singapore (SG)

(72) Inventors: Gary D. Cudak, Wake Forest, NC (US); William M. Megarity, Raleigh, NC (US); Luke D. Remis, Raleigh, NC (US); Christopher L. Wood, Chapel Hill, NC (US)

(73) Assignee: Lenovo Enterprise Solutions (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 14/985,813

(22) Filed: Dec. 31, 2015

(51) Int. Cl.
*A61L 2/10* (2006.01)
*G06F 19/00* (2011.01)

(52) U.S. Cl.
CPC ............ *A61L 2/10* (2013.01); *G06F 19/3493* (2013.01)

(58) Field of Classification Search
USPC ............ 250/455.11, 454.11, 504 R; 134/1.1
See application file for complete search history.

(56) References Cited

U.S. PATENT DOCUMENTS 8,994,056 B2 * 3/2015 Edwards ................ G09F 9/33
257/100
2004/0100437 A1 * 5/2004 Hunter ............ G02F 1/133617
345/102
2016/0093412 A1 * 3/2016 Liao ........................ G21K 5/02
250/221

OTHER PUBLICATIONS

Sensor Electronic Technology, Inc. (SETi), "Flow Many Germs do you carry with you?" UV LED Cell Phone Disinfection, www.s-et.com, Mar. 27, 2015, 2 pages.
Vioguard, "The only FDA approved self-sanitizing keyboard and mouse", www.vioguard.com, 23567-411-RevA 0315, Mar. 27, 2015, 2 pages.

* cited by examiner

*Primary Examiner* — Kiet T Nguyen
(74) *Attorney, Agent, or Firm* — Katherine S. Brown; Jeffrey L. Streets (57) ABSTRACT

An apparatus includes a display screen including a first array of first light-emitting diodes for emitting visible light and a second array of second light-emitting diodes for emitting ultraviolet light, wherein the second light-emitting diodes are interspersed among the first light-emitting diodes. A method includes a computing device receiving input from a remote server indicating that a surface of the computing device should be disinfected, the computing device detecting that a display screen is in a closed positioning facing the surface, wherein the display screen includes an array of light-emitting diodes for emitting ultraviolet light, and controlling operation of the light-emitting diodes to disinfect the surface in response to the input received. The surface may, for example, be selected from a keyboard, a touchpad, and a cover.

10 Claims, 7 Drawing Sheets

DISPLAY SCREEN WITH LIGHT-EMITTING DIODES FOR ULTRAVIOLET DISINFECTION

BACKGROUND

1. Field of the Invention

The present invention relates to systems and method for disinfecting a surface, such as a keyboard or display screen.

2. Background of the Related Art

The ordinary use of computer keyboards and touchscreens can lead to an accumulation of pathogens growing on these surfaces. These pathogens may then increase in number or be spread between individuals that share use of the keyboards and touchscreens. A "pathogen" may be any infectious agent that can cause disease, such as a virus, bacterium, prion, fungus, viroid or parasite.

Although it is desirable to periodically clean the surfaces of a keyboard and touchscreen, doing so can be difficult and tedious, while posing a threat of damage to the devices. In particular, a keyboard includes a large number of individual surfaces and mechanical connections that can become displaced or damaged due to physical forces, and electrical components that can be damaged by corrosive fluids or excessive amounts of fluids.

Current disinfection methods involve either wiping the keyboard with a cloth carrying some type of disinfectant chemical or manually moving a UV light-emitting wand over the keyboard. The wiping method leaves many areas untouched and some users are uncomfortable wiping their keyboards with a liquid (or gel). The UV light method is rarely used and requires purchase and care of a separate device. Still, neither of these cleaning methods will prevent the spread of pathogens if a user will not take the time to use them properly.

BRIEF SUMMARY

One embodiment of the present invention provides an apparatus comprising a display screen including a first array of first light-emitting diodes for emitting visible light and a second array of second light-emitting diodes for emitting ultraviolet light, wherein the second light-emitting diodes are interspersed among the first light-emitting diodes.

Another embodiment of the present invention provides a method comprising a computing device receiving input from a remote server indicating that a surface of the computing device should be disinfected, the computing device detecting that a display screen is in a closed positioning facing the surface, wherein the display screen includes an array of light-emitting diodes for emitting ultraviolet light, and controlling operation of the light-emitting diodes to disinfect the surface in response to the input received.

DETAILED DESCRIPTION

One embodiment of the present invention provides an apparatus comprising a display screen including a first array of first light-emitting diodes for emitting visible light and a second array of second light-emitting diodes for emitting ultraviolet light, wherein the second light-emitting diodes are interspersed among the first light-emitting diodes.

Optionally, the first array of first light-emitting diodes for emitting visible light may include light-emitting diodes that emit red light, light-emitting diodes that emit green light and light-emitting diodes that emit blue light. However, it should be recognized that red, green and blue light-emitting diodes may be housed in a single package and referred to as a red, green, blue light-emitting diode (RGB LED). Regardless of packaging, control over red, green and blue light can produce any desired color on one picture element (pixel) of the display. Independently, the light-emitting diodes for emitting ultraviolet light may include a semiconductor material selected from diamond, boron nitride, aluminum nitride, aluminum gallium nitride and aluminum gallium indium nitride.

The first array and the second array may be formed on a single panel, or the first array and the second array may be formed on separate panels, one in front of the other. For example, the first array may be formed on a first panel and the second array may be formed on a second panel disposed behind the first panel. Where one panel is disposed behind another panel, a forward panel must include transparent portions to allow the passage of light from the rear panel. In one option, the display screen may further include a liquid crystal display panel in parallel with, and aligned with, the first array and the second array. For example, the liquid crystal display may govern the brightness of the display. In another option, the display screen may be a touchscreen.

In yet another option, the first array of first light-emitting diodes for emitting visible light may include a greater number of light-emitting diodes than the second array of second light-emitting diodes for emitting ultraviolet light. The manner and spacing in which the second light-emitting diodes are interspersed among the first light-emitting diodes may vary.

In another embodiment, the apparatus may further include a physical computer keyboard having a connector for securing the display screen in an open position for displaying visible images to a user using the first array and in a closed position for exposing the computer keyboard to ultraviolet light using the second array. The configuration of a physical computer keyboard connected to a display screen is common to a laptop computer and various tablet computers that are securable to a separate physical keyboard. In a preferred option, the second array of second light-emitting diodes for emitting ultraviolet light are only enabled in response to the display screen being in the second closed position. The open or closed position of the display screen may be sensed using various detectors or sensors, such as position sensors and proximity sensors.

In an alternative embodiment, the display screen may a touchscreen of a tablet computer or a mobile communication device, such as a smartphone. Accordingly, the second array of second light-emitting diodes for emitting ultraviolet light may only be enabled in response to a cover being in a closed position over the display screen. Requiring that the cover be in a closed position may be a safety precaution, but may also serve to enhance disinfection of the cover and the touchscreen itself due to reflection.

Another embodiment of the present invention provides a method comprising a computing device receiving input from a remote server indicating that a surface of the computing device should be disinfected, the computing device detecting that a display screen is in a closed positioning facing the surface, wherein the display screen includes an array of light-emitting diodes for emitting ultraviolet light, and controlling operation of the light-emitting diodes to disinfect the surface in response to the input received. The surface may, for example, be selected from a keyboard, a touchpad, and a cover. It is also possible that the display screen itself will be disinfected. In the discussion and examples of the present invention, the description may be stated in terms of disinfecting a keyboard, but it should be understood that the invention is equally applicable to the disinfection of any surface that is positioned in front of the display screen In various embodiments of the method, the input indicating that a surface of the computing device, such as a keyboard, should be disinfected may contain addition information or limitations that are used by the computing device. In a first example, the input may further identifies an affected geographic region. Accordingly, the method may further comprise determining the location of the computing device, and energizing the light-emitting diodes for emitting ultraviolet light only in response to the location of the computing device being within the affected geographic region. This allows computing devices in a geographic region affected by a pathogenic outbreak to disinfect their keyboard. Furthermore, the input may be received over a wide area network from a third party server storing epidemiology data.

In a second example, the input may further identify a type of pathogen. While some types of bacteria are to be expected to be present on the keyboard at any time, the identified type of pathogen may be involved in a current outbreak and may require more than a standard disinfection routine. Accordingly, the method may further comprise determining an intensity and duration of ultraviolet light necessary to disinfect a surface containing the identified type of pathogen, and energizing the ultraviolet light-emitting diodes for the determined intensity and duration. Optionally, the intensity and duration of ultraviolet light necessary to disinfect the surface of the identified type of pathogen may be obtained from a locally stored list or database of pathogen disinfection data that associates ultraviolet light intensity and duration to each identified pathogen. Preferably, where multiple pathogens are identified, the method will disinfect the surface using the more rigorous of the associated regimen of ultraviolet light intensity and duration. In a third example, the input identifies a recommended intensity and duration of ultraviolet light, with or without identifying the type of pathogen. Therefore, the method may further comprise energizing the light-emitting diodes for emitting ultraviolet light at the recommended intensity for the recommended duration.

While the disinfection with ultraviolet light may wait until the display screen is closed, the method may further display a message to the user indicating the need to close the screen to allow disinfection to proceed. Furthermore, once a disinfection process has begun, an optional aspect of the method may, if allowed by user settings, lock the display screen in a closed position so that the disinfection may be completed. Excess power consumption may be avoided by controlling the ultraviolet light at the identified intensity and duration, rather than some excessive or random amount ultraviolet light.

Optionally, the method may prevent operation of the light-emitting diodes to disinfect the surface in response to the computing device experiencing a period of inactivity greater than a predetermined period of time. This optional step avoids unnecessary disinfection, and an associated power consumption, if the computing device has not been is used and most likely not exposed to the pathogen of concern. A particular beneficial point at which to disinfect the surface, such as a keyboard, is in response to a user logout event, such that the surface is disinfected prior to a possible use by another user.

Yet another embodiment of the present invention provides a computer program product comprising a computer readable storage medium having non-transitory program instructions embodied therewith, wherein the non-transitory program instructions are executable by a processor to cause the processor to perform a method. The method comprises receiving input from a remote server indicating that a surface of a computing device should be disinfected, detecting that a display screen of the computing device is in a closed positioning facing the surface, wherein the display screen includes an array of light-emitting diodes for emitting ultraviolet light, and controlling operation of the light-emitting diodes to disinfect the keyboard in response to the input received.

The foregoing computer program products may further include program instructions for implementing or initiating any one or more aspects of the methods described herein. Accordingly, a separate description of the methods will not be duplicated in the context of a computer program product.

Figure 1A:
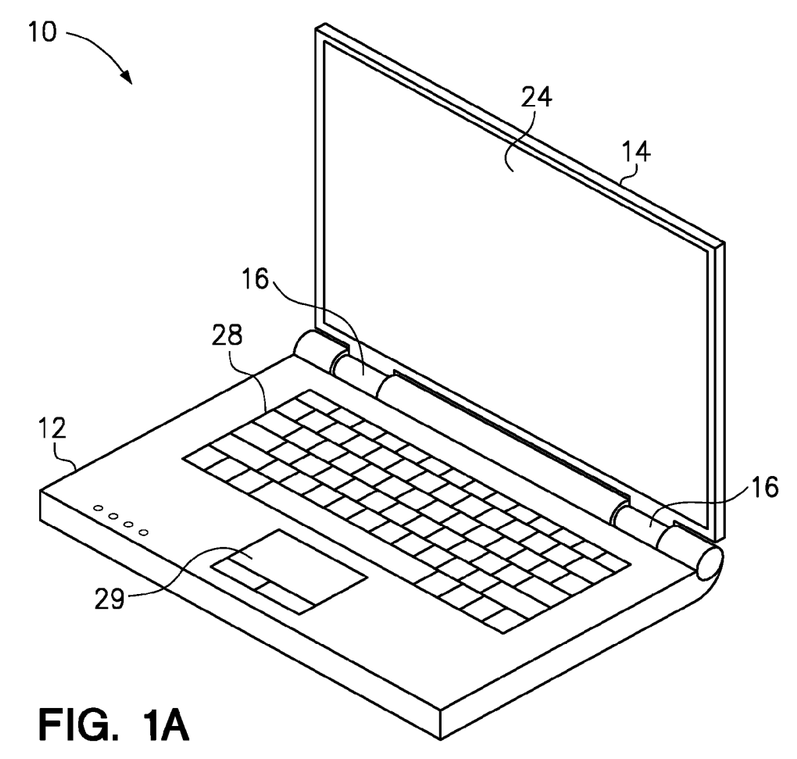
FIGS. 1A and 1B are diagrams of a laptop computer with the display screen in an open position and a closed position, respectively.
Figure 1B:
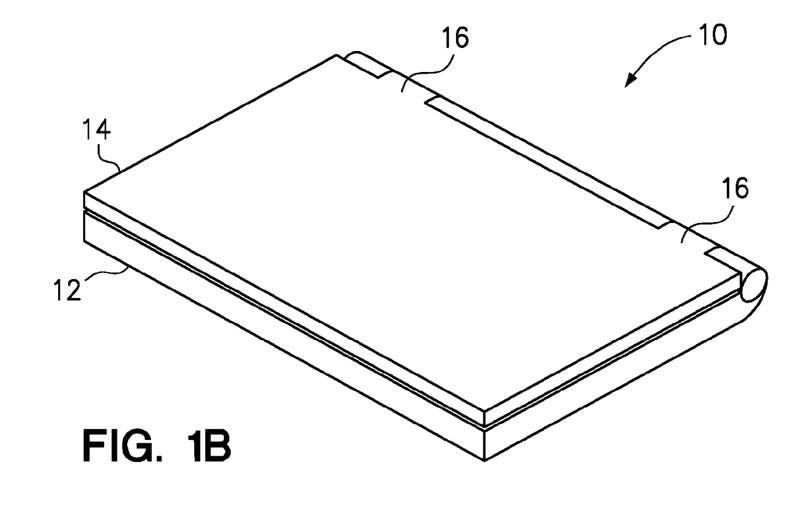

FIGS. 1A and 1B are diagrams of a laptop computer 10 with the display screen 24 in an open position and a closed position, respectively. In FIG. 1A, the laptop computer 10 has a main housing or base 12 that includes a keyboard 28 and a track pad 29. The main housing 12 is coupled to a display housing 14 by a pair of hinges 16. Preferably, the hinges 16 provide sufficient friction to support the display housing 14 at any desired angle relative to the main housing 12. As shown in FIG. 1A, the display housing 14 and display screen 24 are in a generally upright and open position for displaying visible images to a user. In FIG. 1B, the same laptop computer 10 is shown with the display housing 14 in a closed position relative to the main housing 12, such that the display screen 24 (not shown) is face-to-face with the keyboard 28 (not shown). This closed position is typically used for storage and transportation of the laptop computer 10, but the present invention also utilizes this closed position for disinfection of the keyboard and/or the display screen.

Figure 2:
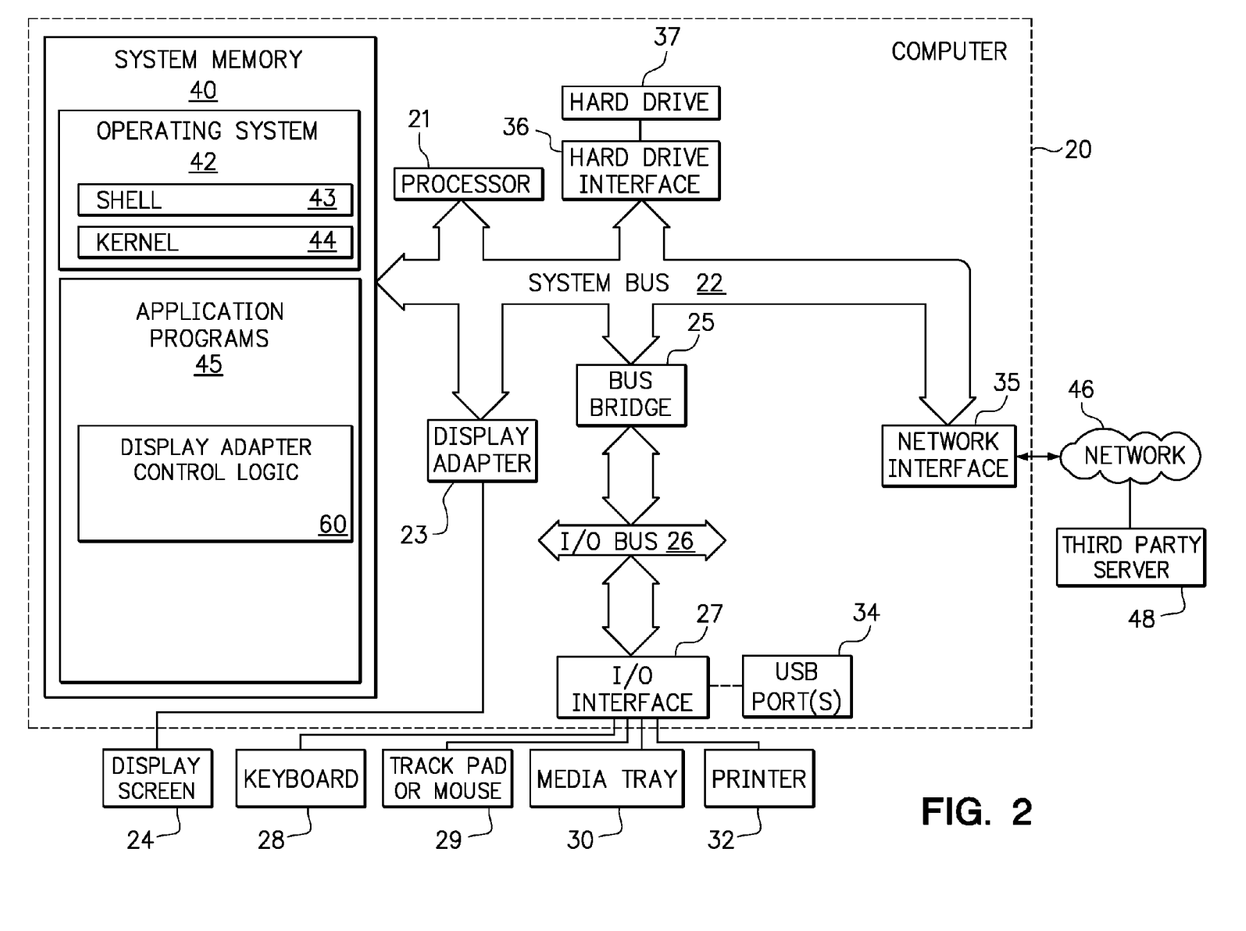
FIG. 2 is a diagram of a computer.

FIG. 2 is a diagram of a computer 20, such as the laptop computer 10 of FIG. 1, which is capable of implementing the methods of the present invention. In this non-limiting example, the computer 20 includes a processor unit 21 that is coupled to a system bus 22. The processor unit 21 may utilize one or more processors, each of which has one or more processor cores. A display adapter 23, which drives/supports a display screen 24, is also coupled to the system bus 22. The system bus 22 is coupled via a bus bridge 25 to an input/output (I/O) bus 26. An I/O interface 27 is coupled to the I/O bus 26 and provides communication with various I/O devices, including a keyboard 28, a trackpad or mouse 29, a media tray 30 (which may include storage devices such as CD-ROM drives, multi-media interfaces, etc.), a printer 32, and USB port(s) 34. As shown, the computer 20 is able to communicate with other network devices, such as a third party server 48, via the network 46 using a network adapter or network interface controller 35.

A hard drive interface 36 is also coupled to the system bus 22. The hard drive interface 36 interfaces with a hard drive 37. In a preferred embodiment, the hard drive 37 communicates with system memory 40, which is also coupled to the system bus 22. System memory includes the lowest level of volatile memory in the compute node 20. This volatile memory may include additional higher levels of volatile memory (not shown), including, but not limited to, cache memory, registers and buffers. Data that populates the system memory 40 includes the operating system (OS) 42 and application programs 45.

The operating system 42 includes a shell 43 for providing transparent user access to resources such as application programs 45. Generally, the shell 43 is a program that provides an interpreter and an interface between the user and the operating system. More specifically, the shell 43 executes commands that are entered into a command line user interface or from a file. Thus, the shell 43, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 44) for processing. Note that while the shell 43 is a text-based, line-oriented user interface, the present invention will equally well support other user interface modes, such as graphical, voice, gestural, etc.

As depicted, the operating system 42 also includes the kernel 44, which includes lower levels of functionality for the operating system 42, including providing essential services required by other parts of the operating system 42 and application programs 45, including memory management, process and task management, disk management, and mouse and keyboard management. The application programs 45 in the system memory of the compute node 20 may include, without limitation, display adapter control logic 60 in accordance with various embodiments of the present invention. One example of the component wear-leveling logic 60 is the method of FIG. 6.

The hardware elements depicted in the computer 20 are not intended to be exhaustive, but rather are representative. For instance, the computer 20 may include alternate memory storage devices such as magnetic cassettes, digital versatile disks (DVDs), Bernoulli cartridges, and the like. These and other variations are intended to be within the scope of the present invention.

Figure 3:
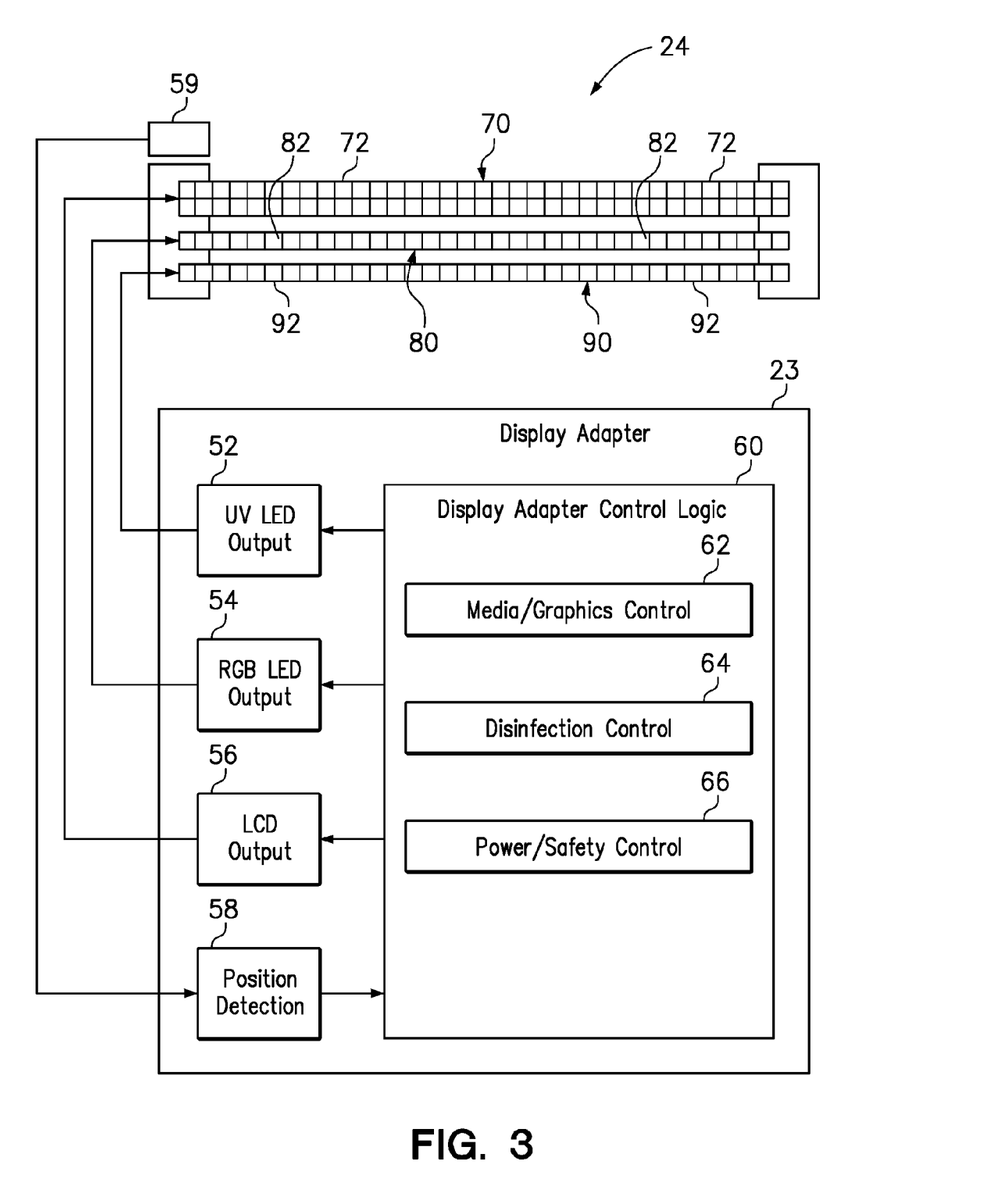
FIG. 3 is a diagram of a display screen and display adapter controlling the display screen.

FIG. 3 is a diagram of a display screen 24 and display adapter 23 controlling the display screen. While the diagram illustrates a liquid crystal display (LCD) screen, the display screen is representative of, and may be substituted with, other display screen configurations disclosed herein. The display screen 24 includes a liquid crystal array 70 including individually addressable liquid crystal elements (LCD elements) 72, a first array 80 of individually addressable light-emitting diodes 82 for emitting visible light, a second array 90 of light-emitting diodes 92 for emitting ultraviolet light, and a display adapter or controller 23. The LCD array 70 includes a layer of liquid crystals between two transparent plates. While the plates may be continuous sheets, the divisions shown represent pixels that are defined by electrodes secured to the two transparent plates and facing the liquid crystal layer.

Each of the individually addressable light-emitting diodes 82 in the first array 80 are aligned with one of the LCD elements 72 and logically associated with the LCD element 72 with which it is aligned. The light-emitting diodes 82 are individually addressable so that any one or more of the light-emitting diodes 82 can be separately controlled to generate more or less light of a given color. According to one embodiment of the invention, each pixel of the display screen 24 may include an LCD element 72 and a light-emitting diode 82 that are all in alignment and logically associated with each other.

The second array 90 of light-emitting diodes 92 for emitting ultraviolet light are formed on a separate panel behind the first array 80. It is not necessary for these light-emitting diodes 92 to be individually addressable, although addressability is within the scope of the invention. Rather, the entire array 90 of light-emitting diodes 92 for emitting ultraviolet light may be turned on and off as a group, preferably with control over the intensity and duration that the light-emitting diodes 92 are energized.

The display adapter or controller 23 includes one or more UV LED output 52, one or more RGB LED output 54, and one or more LCD output 56. These outputs allow the display adapter 23 to communicate with and control the LCD array 70, RGB LEDs 80, and UV LEDs 90. The display adapter control logic 60 includes a media/graphics control module 62, a disinfection control module 64, and a power/safety control module 66. In accordance with one or more embodiments of the present invention, the media/graphics control 62 will control the LCD array 70 and the RGB LED array 80 to produce a visible display when the computer is in use and the display screen is in an open position. Conversely, the disinfection control module 64 will control the UV LED array 90 to disinfect a keyboard and/or an external surface of the display screen itself when the display screen is in a closed position. The display adapter control logic 60 may receive a signal from the position detection input 58 coupled to a detector element 59 that detects the physical position of the display screen 24.

Figure 4A:
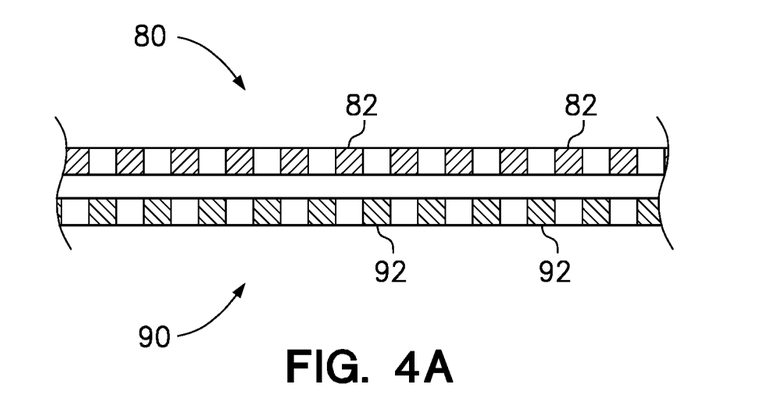
FIGS. 4A-4C are diagrams of display screens having various arrangements of a first array of first light-emitting diodes for emitting visible light and a second array of second light-emitting diodes for emitting ultraviolet light.
Figure 4B:
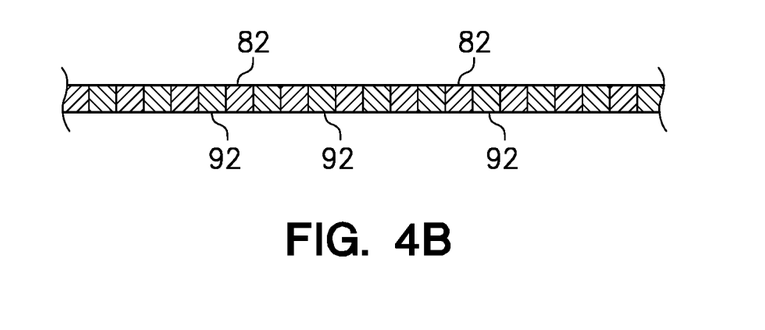
Figure 4C:
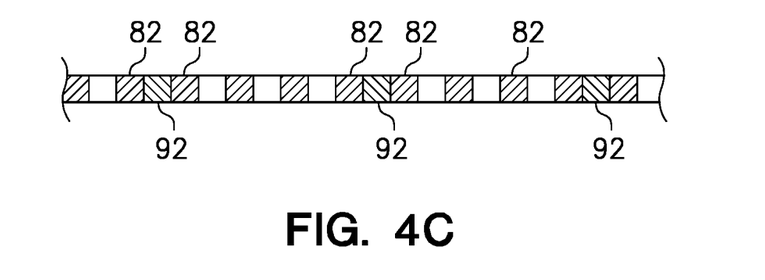

FIGS. 4A-4C are diagrams of display screens having various arrangements of a first array 80 of first light-emitting diodes 82 for emitting visible light and a second array 90 of second light-emitting diodes 92 for emitting ultraviolet light. These various display screens may be used in one or more embodiments of the invention, with or without an LCD panel. In each diagram, the first light-emitting diodes 82 and the second light-emitting diodes 92 are considered to be interspersed. In FIG. 4A, a display screen includes a first upper panel supporting the first array 80 of first light-emitting diodes 82 for emitting visible light and a second lower panel supporting the second array 90 of second light-emitting diodes 92 for emitting ultraviolet light. As shown, the UV LEDs 92 may be offset from the RGB LEDs 82 in order to direct light through transparent regions of the upper panel between the RGB LEDs 82. In FIG. 4B, a display screen includes a single panel supporting both the first array 80 of first light-emitting diodes 82 for emitting visible light and the second array 90 of second light-emitting diodes 92 for emitting ultraviolet light. As shown, the UV LEDs 92 are interspersed in an alternative pattern with the RGB LEDs 82. In a full display screen, the RGB LEDs 82 and the UV LEDs 92 may form a two dimensional matrix pattern. In FIG. 4C, a display screen includes a single panel supporting both the first array 80 of first light-emitting diodes 82 for emitting visible light and the second array 90 of second light-emitting diodes 92 for emitting ultraviolet light. As shown, the UV LEDs 92 are interspersed with the RGB LEDs 82 but there are a greater number of the RGB LEDs 82 than the UV LEDs 92.

Figure 5A:
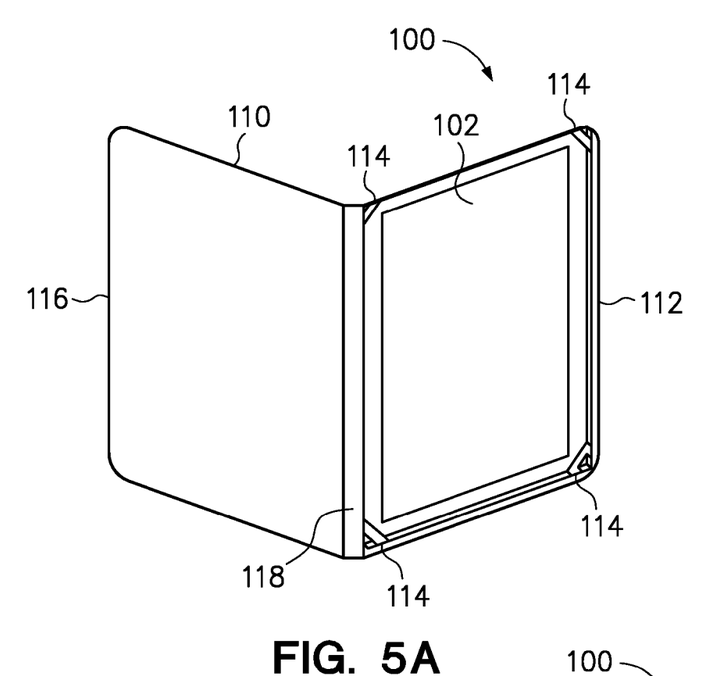
FIGS. 5A and 5B are diagrams of a tablet computer with the touchscreen display in an open position and a closed position, respectively.
Figure 5B:
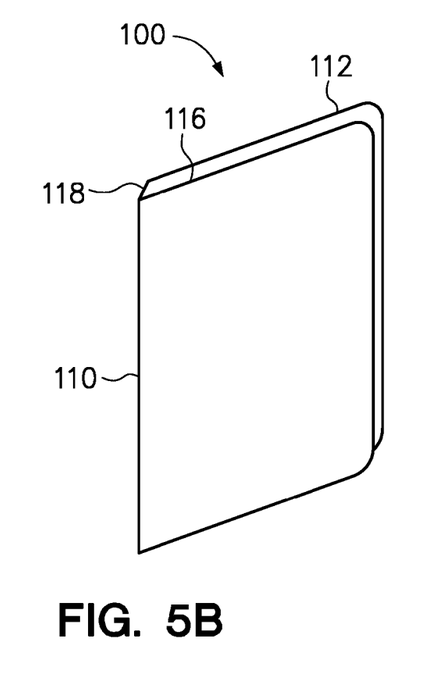

FIGS. 5A and 5B are diagrams of a tablet computer 100 with the touchscreen 102 in an open position and a closed position, respectively. The table computer 100 includes a computing device integrated behind the touchscreen 102. A cover 110 may include a first panel 112 with corner straps 114 for releasably securing the tablet computer 100. A second panel 116 is hinged, such as with a narrow fabric section 118, to the first panel 112. In FIG. 5A, the cover 110 and tablet computer 100 are in an open position in which the RGB LEDs are used to provide a visible display to a user. FIG. 5B, illustrates the same cover 110 in a closed position, with the second panel 116 covering the touchscreen 102, such that the UV LEDs may be used to disinfect the touchscreen 102 are perhaps also the inside cover of the second panel 116 that comes into contact with the touchscreen 102. All other aspects of the present invention previously described in reference to the laptop computer 10 may be similarly implemented in reference to the tablet computer 100. However, the tablet computer 100 used the touchscreen 102 to display a virtual keyboard (not shown), such that disinfecting the virtual keyboard involves exposing the exterior surface of the touchscreen to ultraviolet light from inside the touchscreen.

Figure 6:
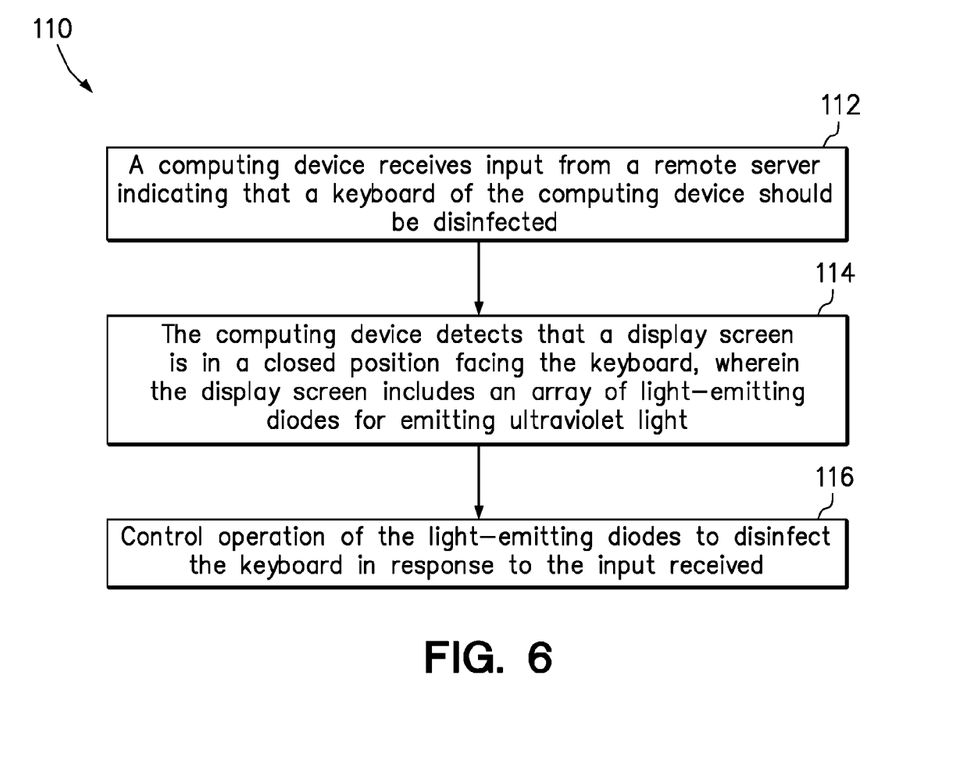
FIG. 6 is a flowchart of a method in accordance with one embodiment of the present invention.

FIG. 6 is a flowchart of a method 110 in accordance with one embodiment of the present invention. In step 112, a computing device receives input from a remote server indicating that a keyboard (or other surface) of the computing device should be disinfected. In step 114, the computing device detects that a display screen is in a closed positioning facing the keyboard, wherein the display screen includes an array of light-emitting diodes for emitting ultraviolet light. Then, in step 116, the method controls operation of the light-emitting diodes to disinfect the keyboard (or other surface) in response to the input received.

Figure 7:
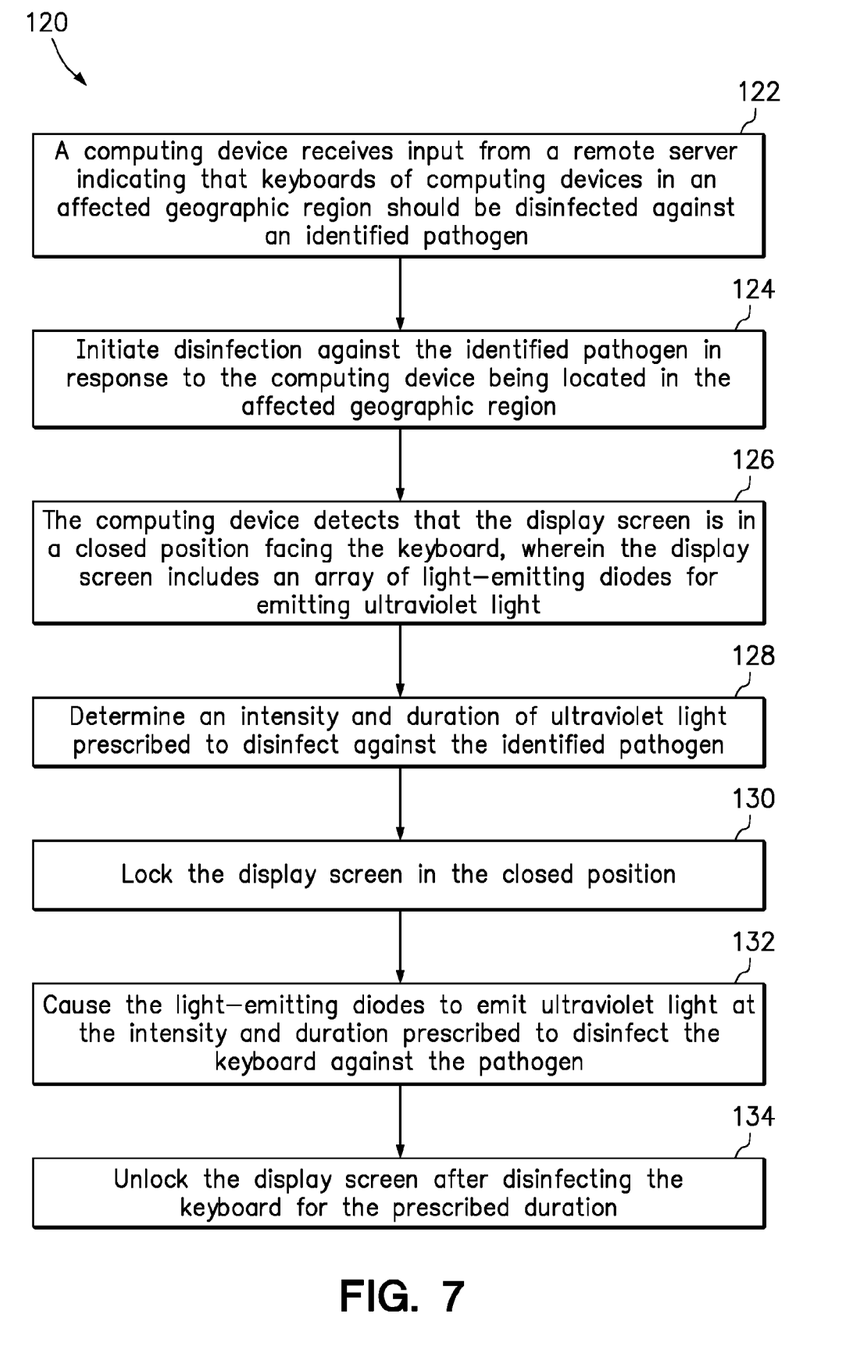
FIG. 7 is a flowchart of a method in accordance with another embodiment of the present invention.

FIG. 7 is a flowchart of a method 120 in accordance with another embodiment of the present invention. In step 122, a computing device receives input from a remote server indicating that keyboards (or another surface) of computing devices in an affected geographic region should be disinfected against an identified pathogen. In step 124, the method initiates disinfection against the identified pathogen in response to the computing device being located in the affected geographic region. In step 126, the computing device detects that the display screen is in a closed position facing the keyboard (or other surface), wherein the display screen includes an array of light-emitting diodes for emitting ultraviolet light. In step 128, the method determines an intensity and duration of ultraviolet light prescribed to disinfect against the identified pathogen. Optionally, this determination may include accessing a list that associates the identified type of pathogen with an intensity and duration of ultraviolet light. In step 130, the display screen is locked in the closed position. In step 132, the method causes the light-emitting diodes to emit ultraviolet light at the intensity and duration prescribed to disinfect the keyboard (or other surface) against the pathogen. Then, in step 134, the display screen is unlocked after disinfecting the keyboard (or other surface) for the prescribed duration.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, and/or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An apparatus, comprising:
a display screen including a first array of first light-emitting diodes for emitting visible light and a second array of second light-emitting diodes for emitting ultraviolet light, wherein the second light-emitting diodes are interspersed among the first light-emitting diodes.

2. The apparatus of claim 1, wherein the first array and the second array are formed on a single panel.

3. The apparatus of claim 1, wherein the first array is formed on a first panel and the second array is formed on a second panel behind the first panel.

4. The apparatus of claim 1, wherein the display screen further includes a liquid crystal display panel in parallel with, and aligned with, the first array and the second array.

5. The apparatus of claim 1, wherein the first array of first light-emitting diodes for emitting visible light includes light-emitting diodes that emit red light, light-emitting diodes that emit green light and light-emitting diodes that emit blue light.

6. The apparatus of claim 1, wherein the first array of first light-emitting diodes for emitting visible light includes a greater number of light-emitting diodes than the second array of second light-emitting diodes for emitting ultraviolet light.

7. The apparatus of claim 1, further comprising:
a physical computer keyboard having a connector for securing the display screen in an open position for displaying visible images to a user using the first array and in a closed position for exposing the computer keyboard to ultraviolet light using the second array.

8. The apparatus of claim 7, wherein the second array of second light-emitting diodes for emitting ultraviolet light is only enabled in response to the display screen being in the closed position.

9. The apparatus of claim 1, wherein the display screen is a touchscreen.

10. The apparatus of claim 1, wherein the light-emitting diodes for emitting ultraviolet light include a semiconductor material selected from diamond, boron nitride, aluminum nitride, aluminum gallium nitride and aluminum gallium indium nitride.

* * * * *